(12) United States Patent
Beale et al.

(10) Patent No.: US 9,662,510 B2
(45) Date of Patent: May 30, 2017

(54) APPARATUS AND METHOD FOR THE TREATMENT OF DERMATOLOGICAL DISEASES OR CONDITIONS

(75) Inventors: Gary Beale, Stirling (GB); Eamon McErlean, Alloa (GB)

(73) Assignee: Emblation Limited (GB)

( * ) Notice: Subject to any disclaimer, the term of this patent is extended or adjusted under 35 U.S.C. 154(b) by 785 days.

(21) Appl. No.: 13/183,759

(22) Filed: Jul. 15, 2011

(65) Prior Publication Data

US 2012/0016356 A1    Jan. 19, 2012

Related U.S. Application Data

(60) Provisional application No. 61/365,447, filed on Jul. 19, 2010.

(51) Int. Cl.
 *A61N 5/02* (2006.01)
 *A61N 5/06* (2006.01)
 *A61N 5/04* (2006.01)

(52) U.S. Cl.
 CPC ........... *A61N 5/0624* (2013.01); *A61N 5/025* (2013.01); *A61N 5/04* (2013.01); *A61N 5/0616* (2013.01)

(58) Field of Classification Search
 USPC .................................................. 607/96–114
 See application file for complete search history.

(56) References Cited

U.S. PATENT DOCUMENTS

| | | | |
|---|---|---|---|
| 6,104,959 A | 8/2000 | Spertell | |
| 7,211,411 B2 | 5/2007 | Neefe et al. | |
| 7,292,893 B2 | 11/2007 | Hoenig et al. | |
| 2003/0225441 A1* | 12/2003 | Boynton et al. | 607/104 |
| 2005/0251231 A1* | 11/2005 | Goldberg | 607/89 |
| 2006/0020312 A1* | 1/2006 | Eggers et al. | 607/103 |
| 2008/0149100 A1* | 6/2008 | Van Holst et al. | 128/204.17 |
| 2010/0010480 A1* | 1/2010 | Mehta et al. | 606/9 |
| 2010/0114086 A1* | 5/2010 | Deem et al. | 606/33 |
| 2010/0211059 A1* | 8/2010 | Deem et al. | 606/33 |

OTHER PUBLICATIONS

Choi et al. "Short-Term Heat Exposure Inhibits Inflammation by Abrogating Recruitment of and Nuclear Factor-κB Activation in Neutrophils Exposed to Chemotactic Cytokines." The American Journal of Pathology, Feb. 2008, vol. 172, No. 2, pp. 367-377.

De Pomerai et al. "Growth and maturation of the nematode Caenorhabditis elegans following exposure to weak microwave fields." Enzyme and Microbial Technology, Jan. 2002, vol. 30, No. 1, pp. 73-79.

Fausch et al. "Human Papillomavirus Can Escape Immune Recognition through Langerhans Cell Phosphoinositide 3-Kinase Activation." The Journal of Immunology, Jun. 1, 2005, vol. 174, No. 11, pp. 7172-7178.

(Continued)

*Primary Examiner* — Joseph Stoklosa
*Assistant Examiner* — Adam Avigan
(74) *Attorney, Agent, or Firm* — Sheridan Ross P.C.

(57) ABSTRACT

The invention provides methods and apparatus for the treatment of dermatological conditions, including, for example, viral infections, microbial infections, cancers, dermatological conditions and particularly infections of the skin caused by human papillomavirus (HPV).

22 Claims, 9 Drawing Sheets

(56) References Cited

OTHER PUBLICATIONS

Gao et al. "Non-ablative controlled local hyperthermia for common warts." Chinese Medical Journal, 2009, vol. 122, No. 17, pp. 2061-2063.
Kashima et al. "Polymerase chain reaction identification of human papillomavirus DNA in CO2 laser plume from recurrent respiratory papillomatosis." Otolaryngol Head Neck Surgery, Feb. 1991, vol. 104, No. 2, pp. 191-195.
Li et al. "Detection with the Polymerase Chain Reaction of Human Papillomavirus DNA in Condylomata Acuminata Treated with CO2 laser and Microwave." International Journal of Dermatology, Mar. 1995, vol. 34, No. 3, pp. 209-211.
Lipke "An Armamentarium of Wart Treatments," Clinical Medicine & Research, Dec. 2006, vol. 4, No. 4, pp. 273-293.
Ogura et al. "Microwave hyperthermia treatment increases heat shock proteins in human skeletal muscle," British Journal of Sports Medicine, 2007, vol. 41, pp. 453-455.
Skitzki et al. "Hyperthermia as an immunotherapy strategy for cancer." Current Opinion in Investigational Drugs, Jun. 2009, vol. 10, No. 6, pp. 550-558.
Tonomura et al. "Effects of Heat Stimulation via Microwave Applicator on Cartilage Matrix Gene and HSP70 Expression in the Rabbit Knee Joint." Journal of Orthopaedic Research, Jan. 2008, vol. 26, No. 1, pp. 34-41.

* cited by examiner

APPARATUS AND METHOD FOR THE TREATMENT OF DERMATOLOGICAL DISEASES OR CONDITIONS

CROSS REFERENCE TO RELATED APPLICATION

This application claims the benefit of priority under 35 U.S.C. §119(e) to U.S. Provisional Patent Application Ser. No. 61/365,447 filed Jul. 19, 2010, which is incorporated herein by reference.

FIELD OF THE INVENTION

The present invention provides methods and apparatus for the treatment of dermatological diseases and/or conditions, including, for example, viral infections, microbial infections, cancers, dermatological conditions and particularly infections of the skin caused by human papillomavirus (HPV)

BACKGROUND

The HPV virus is highly contagious and is typically treated using cryotherapy, salicylic acid, laser surgery silver nitrite, RF ablation, homeopathy, hypnosis, adhesive tape occlusion and various other treatments none of which are currently satisfactory in providing a rapid, reliable, repeatable and efficacious treatment. An extensive review of all current HPV treatments has been compiled by Lipke (*Clin Med Res;* 4: 273-93. (2006)) which highlighted that as of 2006 there has been no reported clinical application of microwave treatment.

Some therapies rely upon ablation or removal of HPV infected tissue, however these methods do not treat the underlying HPV infection and the virus may remain in a latent state which risks further recurrence of the disease. A Quiescent HPV infection can exist within the body for an extended duration (in some case years) before reoccurrence takes place. HPV Lesions such as warts or verrucae are undetected by the immune system preventing their removal until such time as the immune system identifies the virus. Once this occurs the papilloma caused by the virus has been known to spontaneously resolve.

A few HPV strains (HPV5, 8, 16, 18, 30, 31, 33, 35, 39, 40) are known to be malignant with some strains causing cervical cancer which if diagnosed early is treatable.

It is known that microwave hyperthermia (elevated heating) can be used to ablate tissue and cells and this has also been shown to damage the HPV virus. In et al. (*Int J Dermatol* 1995:34:209-211. (1995)) teaches that in vitro exposure of excised condylomata acuminate to microwave energy produces more HPV DNA damage than exposure to CO2 laser.

A number of treatments have attempted to use heat to elevate the temperature of HPV infected tissue. Heat denatures the virus by destroying the shell of the viral particles exposing the antigenic site within the viral structure. The denatured viral particles are collected by sub dermal macrophages and lymphocytes which lead to the immune system producing antibodies to target remaining viruses thus eliminating the systemic HPV infection for that particular strain of the virus.

The deposition of energy and thus treatment efficacy using heat is significantly affected by the delivery modality chosen e.g. $CO_2$ laser targets the superficial surface tissue layers and does not penetrate deeply. Likewise RF ablation is not focused and relies upon grounding paths through the body. Kashima et al. (*Otolaryngol Head Neck Surg* 104(2):191-5 (1991)) teach that these methods also carry the risk of infecting those applying the treatment as the smoke plume ejected by the high energy vaporization of tissue is known to carry HPV virus particles which can infect the respiratory tract.

Microwave radiation can easily penetrate deeply within the epidermal layers to the dermis. The HPV virus is known to reside in the stratum basale and is replicated in the stratum spinosum and stratum granulosum. In very rare cases recurrent HPV infections have had virus particles found within the dermis. Microwave radiation can heat deeper layers resulting in a superior deposition of energy within the lesion. Additionally microwave energy causes heating and gradual desiccation of tissue without generating the harmful smoke plume associated with high energy vaporization.

It is established that heat shock proteins (HSP) are produced in response to various tissue stresses or damage resulting from physical or environmental influences. Heat shock proteins are a class of functionally related proteins whose expression is increased when cells are exposed to elevated temperatures or other stress. It has been suggested that the heat shock proteins may protect the cells from other stressors or against further damage. Heat shock proteins are also involved in antigen presentation, steroid receptor function, intracellular trafficking, nuclear receptor binding, and apoptosis. Typically exposure of cells to a heat shock temperature of 42 degrees C. results in transient activation of heat shock factor (HSF). The DNA-binding activity increases, plateaus, and dissipates, during which the intracellular levels of heat shock protein increase. Heat shock proteins can perform specific functions, for example extracellular and membrane bound heat-shock proteins, especially HSP70 are involved in binding antigens and presenting them to the immune system.

The upregulation of the heat shock proteins is a principle part of the heat shock response and is primarily induced by the heat shock factor. Cellular stresses, such as increased temperature, can cause proteins in the cell to denature. Heat shock proteins bind to the denatured proteins and dissociate from HSF to form trimers and translocate to the cell nucleus to activate transcription resulting in the production of new heat shock proteins which bind to more denatured cells.

In research into the physiological heating effects of electromagnetic fields, high frequency microwave energy (existing between 500 MHz to 200 GHz) has been reported to thermally produce elevated levels of specific heat shock proteins in tissue for example Ogura, *British Journal of Sports Medicine* 41, 453-455. (2007)) teaches that HSP90, HSP72, HSP27 levels are significantly higher in heated vastus lateralis muscle compared with unheated controls. Tonomura et al. (*J Orthop Res.* 26(1):34-41. (2008)) teach that in vivo HSP70 expression in rabbit cartilage increases with the application of moderate levels of microwave power (20-40 W). Additionally de Pomerai et al. (*Enzyme and Microbial Technology* 30, 73-79 (2002)) teaches that prolonged exposure to weak microwave fields (750-1000 MHz, 0.5 W) at 25° C. induces a heat-shock response in transgenic *C. elegans* strains carrying HSP16 reporter genes.

In other unrelated research, U.S. Pat. No. 7,211,411 teaches that HPV can be treated using vaccines containing heat shock proteins as immunologic adjuvants (HSPs). These vaccines fuse specific heat shock protein elements (e.g. HSP60, HSP65. HSP70) with immunostimulatory or antigenic HPV fragments, (e.g. the HPV E7 protein) to invoke a potent immune response to the HPV virus however the vaccine is limited to the strain of the virus used of which more than 100 have been identified. It has been speculated that HSPs may also be involved in binding with protein fragments from dead malignant cells and highlighting them to the immune system thus boosting the effectiveness of the vaccine, e.g. Oncophage (Antigenics Inc, Lexington, Mass.).

Heat shock proteins not only carry antigens but can also induce naturation of dendritic cells, resulting in a more efficient antigen presentation. It is known that hyperthermia can promote the activation of the Langerhans cells. Langerhans cells are the dendritic cells of the skin which continuously monitor the extracellular matrix of the skin and capture, uptake and process antigens to become antigen presenting cells (APC's). Particles and antigens are carried to draining lymph nodes for presentation to T lymphocytes. T cells release chemokines which cause the skin to be infiltrated by neutrophils, resulting in a swelling response which has been observed by Gao et al. (*Chin Med J* (*Engl*), 122(17):2061-3 (2009)) to occur before resolution of a HPV infection.

Hyperthermia also increases the expression of key adhesion molecules in secondary lymphoid tissues. Additionally hyperthermia can also act directly on lymphocytes to improve their adhesive properties. Hyperthermia increases the intravascular display of homeostatic chemokines, and certain inflammatory chemokines which have been proposed by Skitzki et al. (*Curr Opin Investig Drugs*, 10(6):550-8 (2009)) to be classical HSP's based on their regulation by HSP transcription factors It has been observed by Fausch et al. (*J. Immunol.* 174:7171-7178 (2005)) that HPV can escape immune system recognition through Langerhans cell Phosphoinositide 3-Kinase activation (PI3-K). The inhibition of PI3-K allows Langerhans cells to initiate a potent HPV-specific response. Mild hyperthermia involving temperature spiking to mimic fever has been shown by Choi et al, (*Am J Pathol* 172:367-777, 2008) to down-regulate the PI3-K/Akt signalling pathway. Inhibition of PI3-K/Akt by heat also has an inhibitory effect on neutrophil migration which downregulates the inflammatory response.

It is hereby hypothesized that the application of mild localized hyperthermia of a pulsed nature may inhibit PI3-K helping the immune system in identifying the underlying HPV infection promoting Langerhans cells and heat shock proteins to identify and present the HPV virus to the immune system causing a localized inflammatory response followed by eradication.

The emerging understanding is that hyperthermia treatments work at multiple levels via complex complementary mechanisms involving a variety of signalling and trafficking molecules.

SUMMARY

It is proposed here that microwave energy may be employed as a tri-action (heat shock promoting and immune stimulatory, viral denaturing and tissue coagulation) treatment for dermatological conditions where tissue is infected with viral, microbial, or malignant conditions.

The microwave treatment mechanism may thermally instigate the production of heat shock factor HSF thus elevating the level of heat shock proteins in and proximal to infected tissue as a means to invoke an immune response by associating the infected tissue with the elevated heat shock proteins. This localized thermal increase can be achieved using a precise deposition of energy at the location of lesions which is readily achievable using microwave energy. As in the case of HPV this is applicable to any strain of the virus, which overcomes the limitation of a vaccine.

Localised microwave hyperthermia can be used to raise the temperature of the tissue containing the HPV virus thus denaturing the viral particles promoting antibody production to eliminate the virus.

In tissue infected with HPV a network of supply capillaries is generated by the virus to sustain the growth of papillomas such as warts or verrucae. These can be seen as small dark dots close to the surface of the lesion. A number of existing treatments (e.g. cryotherapy, salicylic acid) try to disrupt or damage this blood supply to the lesion in an attempt to alert the immune system to the presence of the virus.

Microwave ablation can be used to coagulate or compromise the function of the blood supply to HPV lesions. The thermal insult and resultant disruption of blood supply to the HPV infected tissue can be used to destroy tissue supported by the capillary feed network resulting in necrosis of the remaining tissue. This technique can also apply to other tissue lesions or growths which have a sustaining blood supply, (e.g. benign growths, skin cancers, neoplasms, moles etc,)

Typically the dielectric properties of materials are measured relative to those of air and referred to as epsilon relative to air (Er) where air is Er=1. The high frequency dielectric properties of tissue infected by HPV have not currently been reported in the literature. The dielectric properties have been measured here and were found to differ considerably from normal tissue. Thus, applicators that electrically match with the range of epsilon relative values may be used to ensure energy is efficiently delivered into the papilloma.

For example in the case of Verruca plantaris, excess keratin changes the dielectric constant of the tissue. The dielectric constant of the measured tissue (sample range 7.5-8.5 GHz) was found to lie between Er 2 to Er 10 for dry tissue. The median Er value was measured at 4.93. The 95% confidence interval for the median was found to lie between Er 4 and Er 6.7.

This is in contrast to normal plantar tissue which was found to range between Er 6 to Er 16 for dry skin, with the median Er value measured at 10.6. The 95% confidence interval for this median lies between Er 8.75 and Er 12.3.

The measured values of epsilon relative were for dry tissue and will differ in value from other HPV lesions elsewhere on the body, e.g. in mucosal tissues which generally have higher values of epsilon relative due to the presence of water which has an Er of 80-34.5 (depending upon temperature). In these instances the Er may be in the range Er 20-40.

The demarcation between the measured values of epsilon relative for various plantar tissue types was found to decrease with increasing measurement frequency which suggests that at higher frequencies the stratum corneum layer dominates the measurements.

As a penetration depth of a few mm may be required a frequency in the range 5.8 GHz to 15 GHz is may be desirable as higher frequencies may not penetrate sufficiently. The power level and energy density of application will also affect the depth of penetration therefore lower frequencies may be used with appropriately designed applicators and treatment profiles.

The present invention is based on the finding that microwave energy may be used to treat dermatological diseases and/or conditions, particularly diseases and/or conditions having a microbial, genetic, allergic, autoimmune and/or malignant (cancerous) aetiology.

In a first aspect, the invention provides a method of treating a dermatological condition and/or disease, said method comprising administering to a subject having or suffering from a dermatological disease and/or condition, a therapeutically effective amount or dose of microwave energy.

In a second aspect, the invention provides microwave energy for use in treating dermatological diseases and/or conditions.

One of skill will appreciate that in order to resolve a dermatological disease and/or condition and/or reduce the symptoms thereof, one or more treatments with microwave energy may be required.

Without wishing to be bound by theory, the inventors hypothesise that the induction of hyperthermia by targeted application of microwave energy, induces the production of heat shock proteins in diseased or damaged tissue. This may lead to the activation of antigen presenting cells (such as dendritic/langerhans cells) which process antigen (including host, microbial or other foreign antigen) for presentation to T cells. Furthermore, the induction of hyperthermia may inhibit phosphoinositide 3-Kinase (PI3-K) in Langerhans cells facilitating the induction of a potent host immune response. Localized thermal increase can be achieved using a precise deposition of energy to a diseased tissue (for example a lesion), readily achievable using microwave energy.

As stated, the term "dermatological diseases and/or conditions" relates to pathological diseases and/or conditions affecting the skin and/or associated tissues. However, the present invention may extend to the treatment of diseases and/or conditions of the integumentary system, including, for example, the mucosal membranes of the respiratory, gastrointestinal and genitourinary systems. One of skill will appreciate that dermatological tissues may comprise epidermal, dermal and/or sub-dermal tissues of the skin as well as other layers, such as the stratum corneum, stratum lucidum, stratum granulosum, stratum spinosum and stratum basale which lie within. Additionally, the term dermatological condition relates to conditions which affect the cosmetic appearance of the skin. Such cosmetic conditions may include the presence of papillomas (warts), marks, scars or calluses.

In one embodiment, the dermatological disease and/or condition is caused or contributed to by a cell/tissue proliferation and/or differentiation disorder such as, for example, cancer. As such, the disease and/or condition to be treated may include skin or cervical cancer. In some cases, the disease and/or condition results in the appearance of benign or malignant lesions. In other embodiments, the dermatological disease and/or condition may result from some uncontrolled accumulation or proliferation of connective tissue or extracellular substance, leading to, for example, keloid lesions and the like.

Dermatological diseases and/or conditions may also include autoimmune, allergic and/or hypersensitivity related pathologies such as, for example, psoriasis, eczema, iethyosis vulgaris, sclerodema and/or lupus.

In other cases, the dermatological disease and/or condition may be caused or contributed to by one or more microbial infections including, for example, fungal, bacterial and/or viral infections. In particular, the invention relates to the treatment of viral skin infections such as those related to or associated with human papillomavirus (HPV). In particular, the present invention finds application in the treatment of papillomas and warts as well as other lesions caused or contributed by a microbial organism such as a virus. In particular, the present invention relates to the treatment of plantar warts otherwise known as verruca plantaris caused by HPV.

One of skill will appreciate that unlike with vaccines which are specific to a particular species of organism and, in some cases, one or a very limited number of specific species strains, microwave energy may be used to treat dermatological diseases and/or conditions irrespective of the species/ strain type. This is particularly important for HPV infections where a large number of different strains are known to be responsible for disease.

As such, one embodiment, of this invention provides a method of treating HPV infections, said method comprising administering a therapeutically effective amount or dose of microwave energy to a subject having or suffering from an HPV infection. In one embodiment, the microwave energy may be directed to a lesion or wart, for example a plantar wart (or verruca), associated with an HPV infection.

The invention also provides microwaves or microwave energy for use in treating HPV infections as well as microwaves for use in treating, resolving, removing or reducing warts, for example plantar warts (or verrucas) associated with an HPV infection.

Again, without wishing to be bound by any particular theory, the inventors suggest that the application of mild localized hyperthermia of a pulsed nature may inhibit PI3-K helping the immune system in identifying the underlying HPV infection promoting Langerhans cells and heat shock proteins to identify and present the HPV virus to the immune system causing a localized inflammatory response.

In a further aspect, the invention provides a method of cosmetically improving the appearance of a part of the body, comprising administering to a subject an amount or dose of microwave energy effective to cosmetically improve the appearance of a part of the body and optionally repeating said treatment until a cosmetically beneficial improvement in appearance has occurred. The method of improving bodily appearance may be used to improve the appearance of a subject's skin and may be used to remove defects of the skin including marks, scars, papillomas (including warts), calluses and the like.

Microwave energy according to this invention may have a frequency of between about 500 MHz and about 200 GHz. In other embodiments, the frequency of the microwave energy may range from between about 900 MHz and about 100 GHz. In particular, the frequency of the microwave energy may range from about 5 GHz to about 15 GHz and in a specific embodiment has a frequency of 8 GHz.

It should be understood that the methods of treatment described herein may require the use of a microwave energy having a single frequency or microwave energy across a range of frequencies.

The invention further provides an apparatus for use in treating dermatological conditions and/or diseases, said apparatus comprising a microwave source for providing microwave energy and means for administering or delivering the microwave energy to a subject to be treated. The apparatus provided by this aspect of the invention may be used in any of the therapeutic methods described herein.

Advantageously, the microwave energy emitted or produced by the apparatus elevates or raises the temperature of the subject to be treated. In one embodiment, the microwave energy causes targeted or localised hyperthermia in a tissue of the subject, including, for example the skin and/or mucosal membrane. The temperature elevation may be localised to the surface of the skin and/or to the epidermal, dermal and/or sub-dermal layers thereof (including all minor layers that lie within).

The apparatus may further comprise means for controlling at least one property of the microwave energy produced by the microwave source. For example the means may control or modulate the power, frequency, wavelength and/or amplitude of the microwave energy. The means for controlling the microwave energy may be integral with the apparatus or separately formed and connectable thereto.

In one embodiment, the microwave energy source may produce microwave energy at a single frequency and/or microwave energy across a range of frequencies. The means for controlling at least one property of the microwave energy may permit the user to select or set a particular microwave or microwaves to be produced by the apparatus and/or the properties of the microwave(s) produced.

The apparatus may further comprise means for monitoring the microwave energy produced or generated by the microwave source. For example, the apparatus may include a display indicating one or more properties of the microwave energy.

In one embodiment, the means for administering or delivering the microwave energy to a subject to be treated comprises an applicator formed, adapted and/or configured to deliver or administer microwave energy to the subject. The inventor has discovered that the dielectric properties of tissue affected by a dermatological disease and/or condition vary with respect to normal, healthy, tissue (i.e. tissue not affected by a dermatological disease and/or condition). As such, the means for delivering microwave energy may electrically match the range of epsilon relative values of the tissue affected by a dermatological disease and/or condition. In this way, it is possible to ensure efficient delivery of the microwave energy to the tissue.

Advantageously, the means for delivering the microwave energy to a subject may comprise a component or part for contact with a subject to be treated. The part or component for contact with the subjected to be treated may be removable such that it can be discarded or sterilised after use. In one embodiment, the means for delivering the microwave energy may comprise a single application element or a hand piece which accepts a removable tip which can either be a single use, disposable component or a reusable component intended to be sterilized between uses. Advantageously, the part or component for contact with the subject to be treated may comprise a reuse mitigation function to prevent accidental or attempted reuse.

In one embodiment, the part or component for contact with the subjected to be treated may be shaped, formed or adapted so as to be compatible with a particular internal or external body part, surface or lesion thereof. For example, the part or component may comprise a domed, curved or enclosing surface, compatible with the physical properties or profile of an internal or external body part, a surface or a lesion thereof, including, for example a papilloma such as a wart or verucca.

The means for delivering the microwave energy to a subject may be connected to the microwave source via a flexible cable. In one embodiment the means for delivering the microwave energy to a subject (i.e. the applicator) may be connected to the microwave source via a flexible cable with locking connections having both microwave and signal data cables and may be reversible to enable connection to either port.

In one embodiment the invention provides an apparatus for delivering microwave energy to infected tissue the apparatus comprising:—a microwave source for providing microwave energy, connectable to a system controller for controlling at least one property of the microwave radiation provided by the microwave source; and a monitoring system for monitoring the delivery of energy and an applicator means, for example an applicator device, for delivering microwave energy, wherein:—the applicator is configured to deliver precise amounts of microwave energy provided by the source at a single frequency or across a range of frequencies.

A further embodiment of this invention provides a method for treating a dermatological disease and/or condition and/or infected tissue, said method comprising the administration or delivery of a therapeutically effective dose or amount of microwave energy to infected or diseased tissue to produce, induce or elevate levels of heat shock factor HSF to stimulate production of heat shock proteins in or near the tissue. In particular, the method for treatment may produce, induce or elevate levels of one or more heat shock proteins selected from the group consisting of HSP90, HSP72, HSP70, HSP65. HSP60, HSP27, HSP16 and any another heat shock protein(s) wherein:—the microwave energy promotes an association between the elevated heat shock proteins and the infected tissue so as to elicit an immune response against the infection.

In a further embodiment of the invention there is provided a method for the treatment of a lesion, said method comprising administering or delivering a therapeutically effective amount or dose of microwave energy to a lesion, wherein the microwave energy cauterises, coagulates, shrinks, blocks, ablates, damages, irritates, inflames or otherwise interferes with the normal operation of the capillaries supplying blood to the lesion. In one embodiment the lesion is a skin lesion including, for example, warts, verrucae, benign growths, skin cancers, moles and the like.

In a further embodiment, the present invention provides a method for the treatment of viral lesion, said method comprising the step of delivering or administering a therapeutically effective amount or dose of microwave energy to the lesion, wherein the microwave energy causes the denaturing of viral particles within the lesion thus exposing antigenic sites stimulating an immune response. In one embodiment the viral lesion is a viral skin lesion such as, for example a warts, verruca, benign growth, cancer and the like.

In another embodiment, the present invention provides a medical treatment regime comprising:—the application of microwave energy to infected skin tissue to purposefully elevate levels of heat shock factor HSF to stimulate production of heat shock proteins in or near the tissue in particular HSP90, HSP72, HSP70, HSP65. HSP60, HSP27, HSP16 and any another heat shock protein(s) wherein the microwave energy promotes an association between the elevated heat shock proteins and the infected tissue with the intention to provoke an immune response against the infection In a further embodiment, the present invention provides a medical treatment regime comprising:—the application of microwave energy into infected skin tissue to purposefully cauterise, coagulate, shrink, block, ablate, damages, irritate, inflame or otherwise interferes with the normal operation of the capillaries supplying blood thus causing necrosis of the lesion.

In another embodiment, the present invention provides a medical treatment regime comprising:—the application of microwave energy into tissue infected with a virus such as human papillomavirus to purposefully denature the viral particles with the intention of exposing antigenic sites thus stimulating an immune response to the virus.

Any feature in one aspect of the invention may be applied to any other aspect of the invention, in any appropriate combination. For example, apparatus features may be applied to method features and vice versa.

BRIEF DESCRIPTION OF THE DRAWINGS

Embodiments of the invention are now described, by way of non-limiting example, and are illustrated in the following figures, in which:—

DETAILED DESCRIPTION OF EMBODIMENTS

Figure 1:
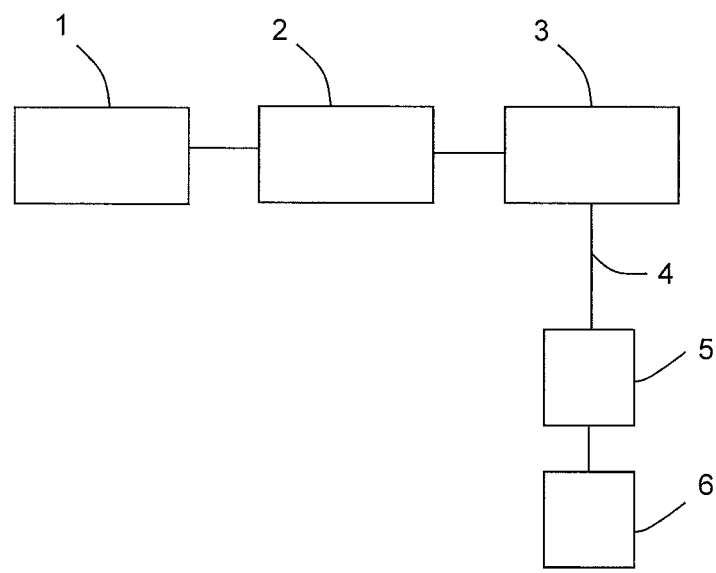
FIG. 1 is a schematic illustration of an embodiment of a microwave treatment system.

An embodiment of a microwave power generator system for medical applications is illustrated in FIG. 1 The apparatus comprising:—a microwave source for providing microwave energy 1, connectable to a system controller 2 for controlling at least one property of the microwave radiation provided by the microwave source; and a monitoring system 3 for monitoring the delivery of energy and an interconnecting cable 4 and an applicator hand piece 5 and a removable applicator means 6, for example an applicator device, for delivering microwave energy, wherein:—the applicator is configured to deliver precise amounts of microwave energy provided by the source at a single frequency or across a range of frequencies.

Figures 2A, 2B:
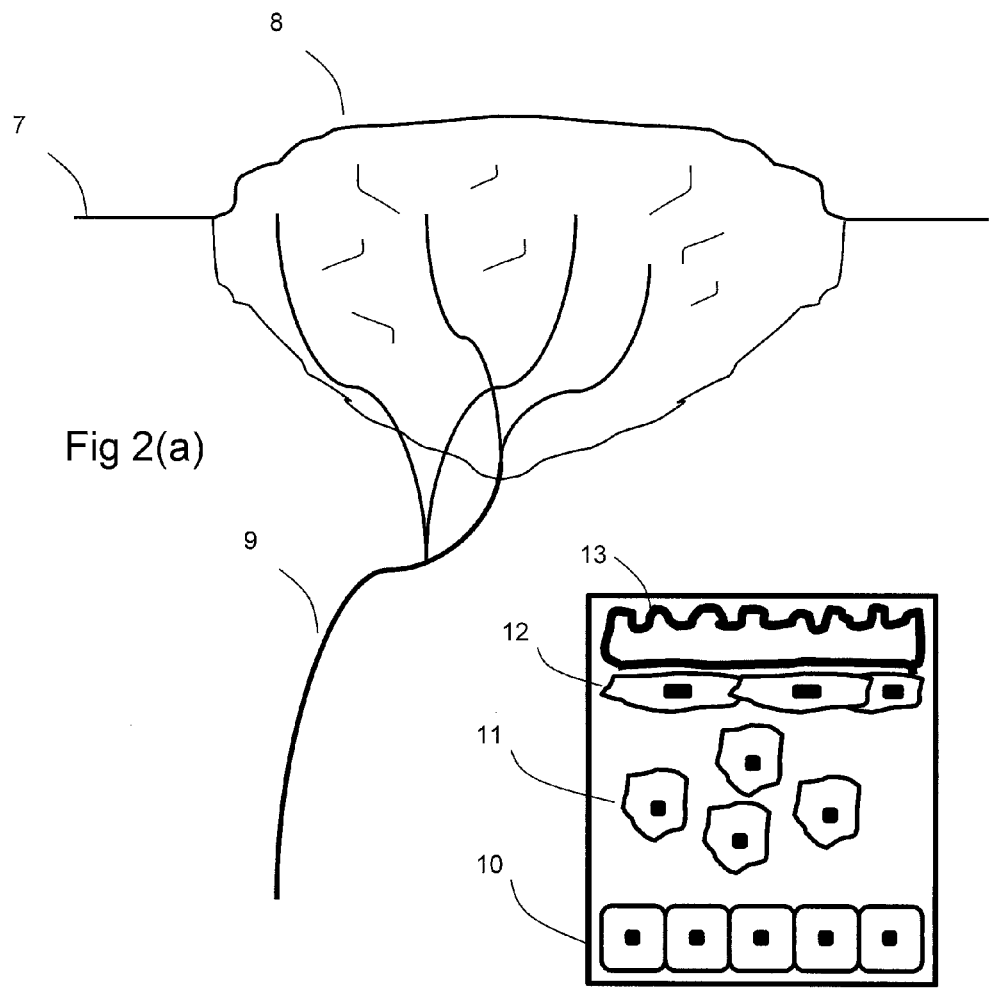
FIG. 2(a) is a schematic illustration of a Papilloma caused by HPV infection.
FIG. 2(b) is a schematic illustration of the terminal differentiation pathway of epidermal cells infected by the HPV virus.

A typical HPV infection is illustrated in FIG. 2(a), this comprises the normal tissue 7, the papilloma surface 8, the capillary feed network 9. The terminal differentiation pathway of epidermal cells infected by the HPV virus is illustrated in FIG. 2(b) basal cells 10 become infected with the HPV virus leading to viral replication in the stratum spinosum 11 followed by assembly of virus particles in the stratum granulosum and release of virus particles in the in the stratum corneum (papilloma surface).

Figure 3:
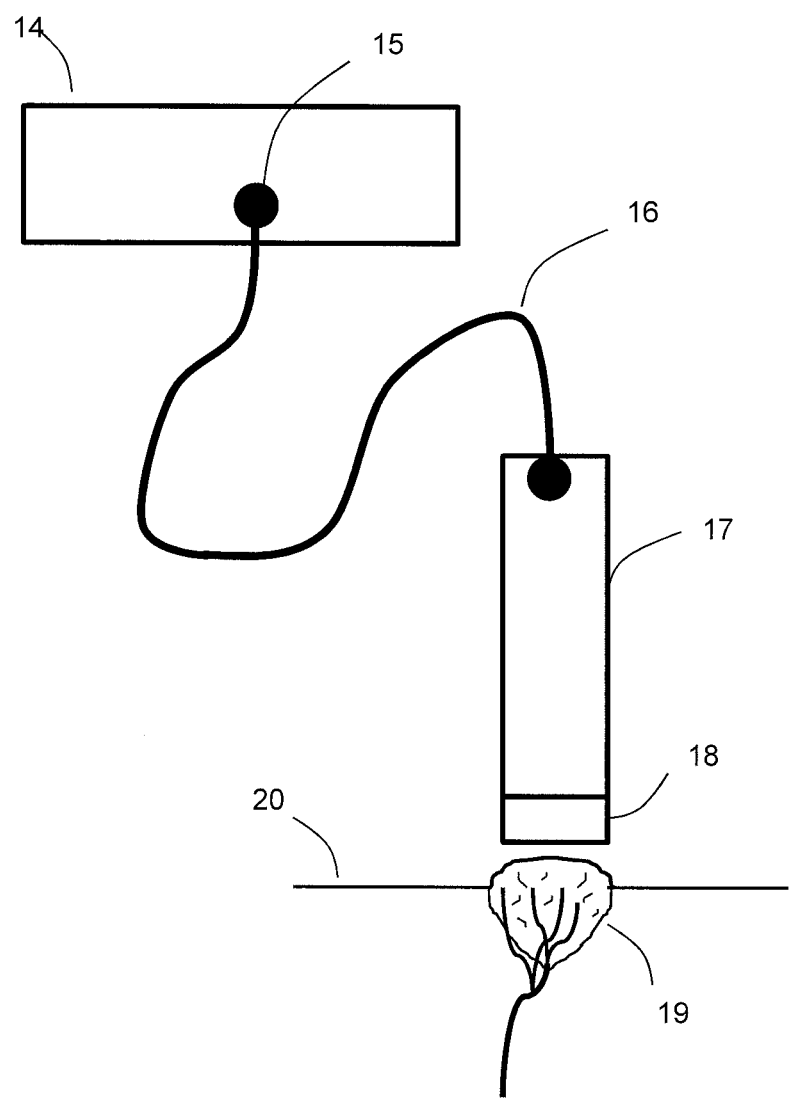
FIG. 3 is a schematic illustration of functional representation of a microwave treatment system for application to treat Papilloma or other dermatological lesions.

FIG. 3 shows the components of an apparatus according to an embodiment of the present invention, the components shown separately for ease of reference. The apparatus comprises a generator system 14 with a locking microwave connection 15 to a flexible microwave cable 16 connected to a hand piece 17 (which may have the same type of locking connection) which accepts an applicator component 19. The applicator component is designed to match to the tissue properties of the papilloma 20 and not match to the normal tissue 18. The cable 16 may include both microwave and signal data cables and may be reversible to enable connection to either port.

Figure 4:
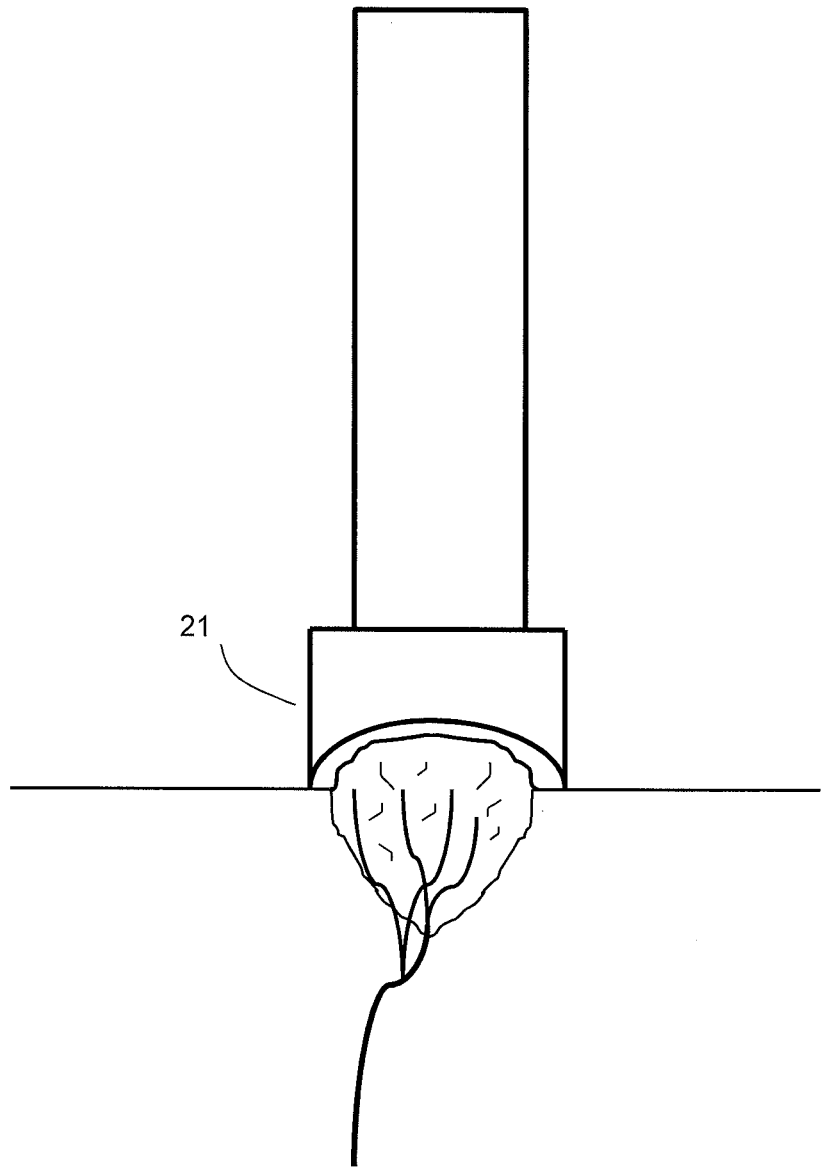
FIG. 4 is a schematic illustration of a microwave treatment system applicator according to an alternative embodiment.

An alternative embodiment of an applicator 21 is illustrated in FIG. 4 with the component having a domed or enclosing surface compatible with raised or curved lesions.

Figure 5:
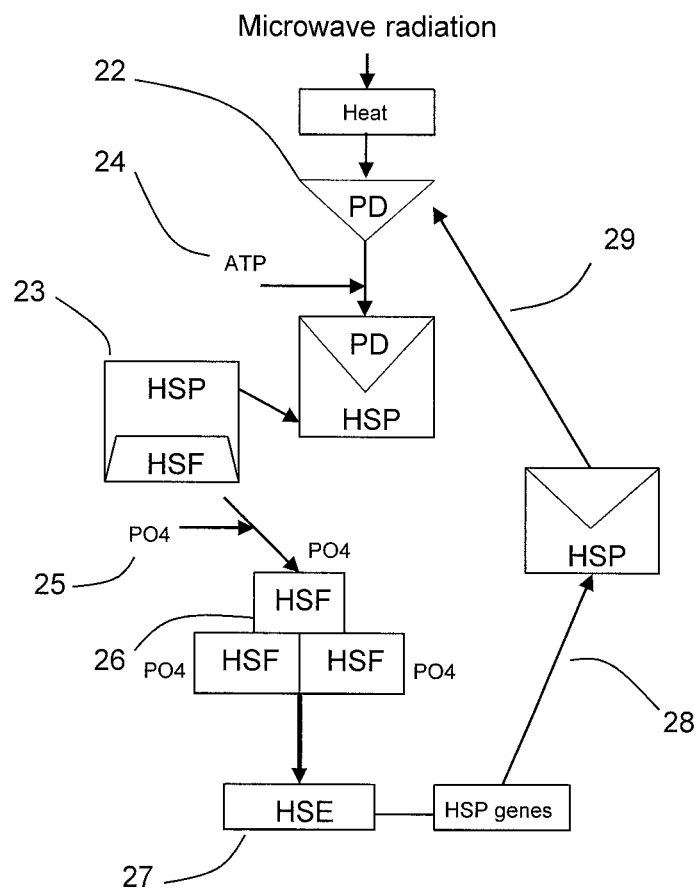
FIG. 5 is a schematic illustration of the microwave activation of the heat shock response.

The method of inducing a microwave heat shock responses is illustrated in FIG. 5. In this illustration microwave radiation creates a thermal stress which results in protein denaturation 22. Heat shock proteins (HSP) are normally bound to heat shock factors (HSF) (23), but dissociate in the presence of denatured proteins (PD). Once dissociated, HSPs bind to the denatured proteins by rapid release. This requires Adenosine Triphosphate (ATP) 24. Further HSPs are generated when HSFs phosphorylate (PO4) (25) and trimerize (26). These trimers bind to heat shock elements (HSE) 27 that are contained within the promoters of the HSPs and generate more protein 28. Newly generated HSPs can then free to bind more denatured proteins 29.

Figure 6A:
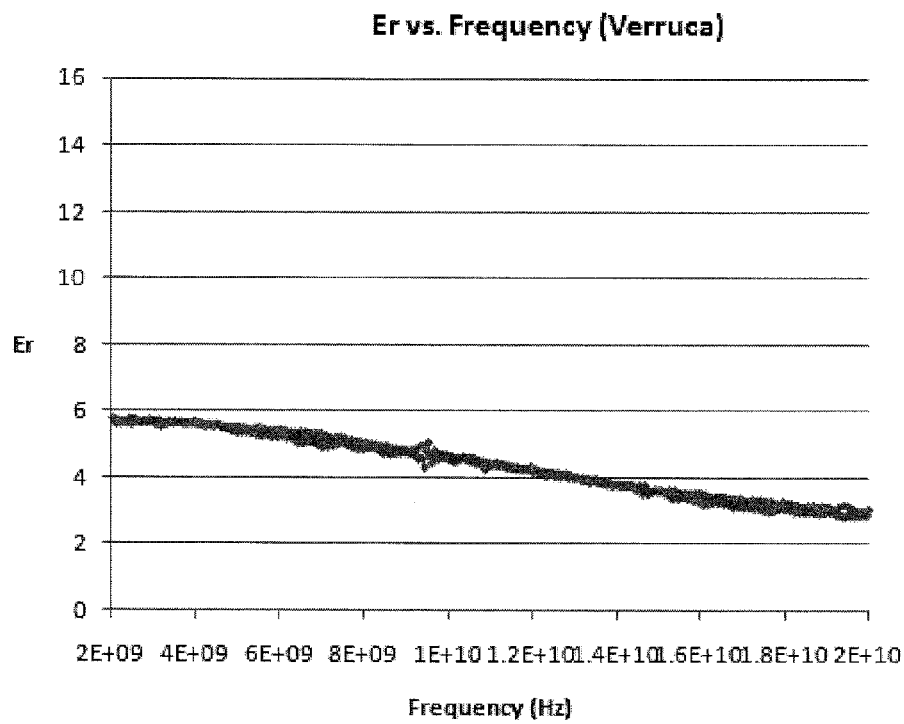
FIG. 6(a) is a schematic illustration of measurement results of Er vs. Frequency for verrucae tissue for a sample population.
Figure 6B:
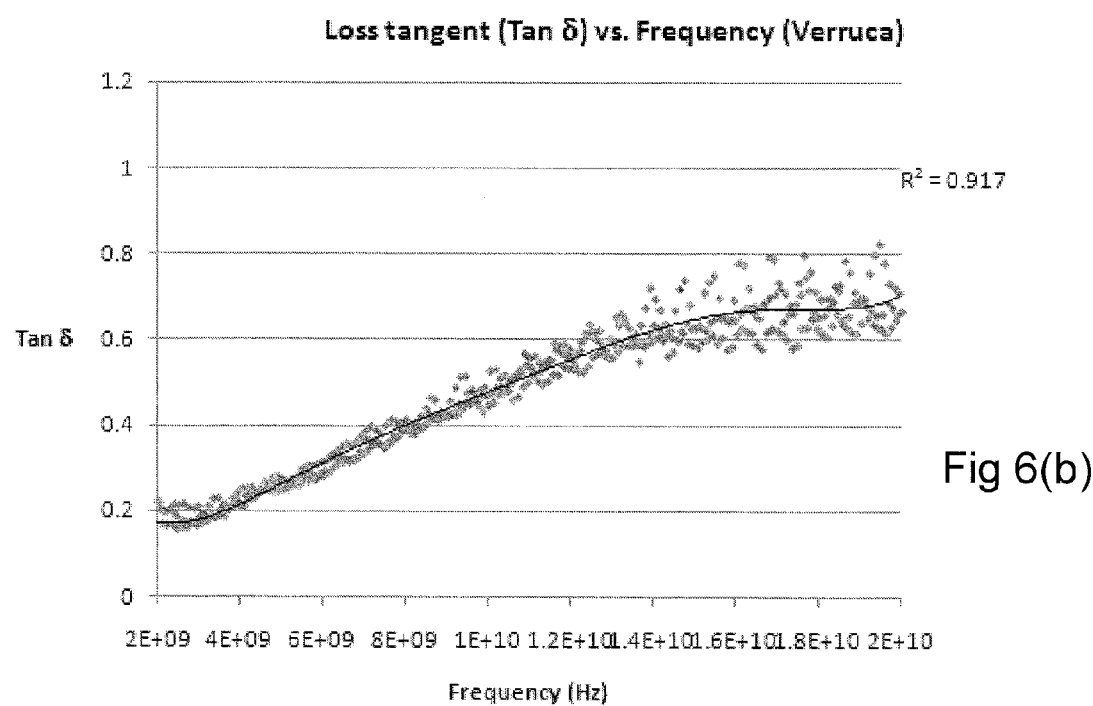
FIG. 6(b) is a schematic illustration of results of Loss tangent vs. Frequency for verrucae tissue for a sample population.

The measured dielectric properties for the sample population median versus frequency of plantar verrucae are reported in FIGS. 6(a) and 6(b). Measured results for ER and loss tangent versus frequency from 2 GHz to 20 GHz are reported. The measurements were made using an Agilent PNA-L Network Analyzer connected to an Agilent 85070E dielectric measurement system with the 85070E Performance Probe Kit (Option 050) measuring from 300 kHz to 20 GHz. Deionised water and air were used as dielectric references for calibration.

Figure 7:
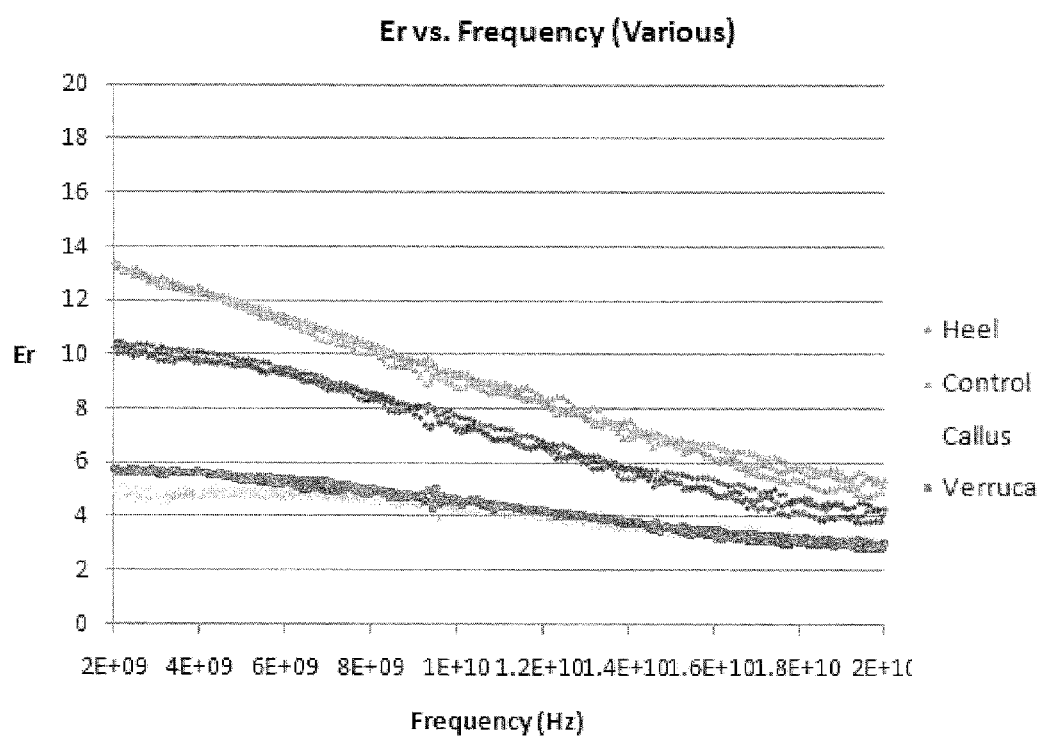
FIG. 7 is a schematic illustration of Er vs. Frequency for various plantar tissues for a sample population.

The measured dielectric properties for the sample population (median taken across the population) versus frequency for various plantar tissues are reported in FIG. 7. Measured results for Er versus frequency from 2 GHz to 20 GHz are reported illustrating demarcation between each tissue type.

Figure 8:
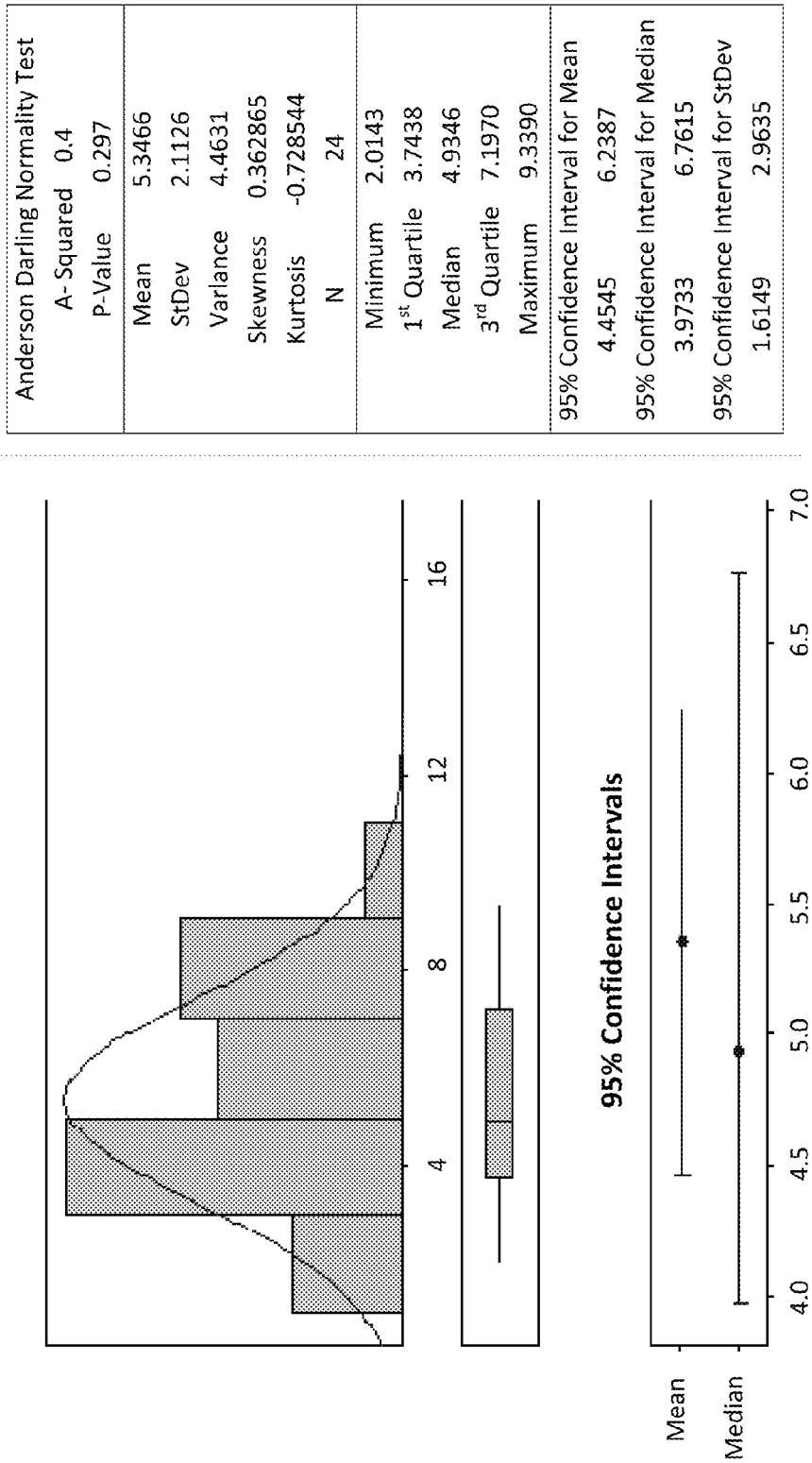
FIG. 8 is a schematic illustration of the statistical analysis of the sample median of verrucae tissue for a sample population.

Statistically analysed dielectric property values taken over a sample population (using the median of the measurement range 7.5-8.5 GHz taken from each sample) for Verrucae tissue is presented in FIG. 8. The median Er value was measured at 4.93 for this dataset.

Figure 9:
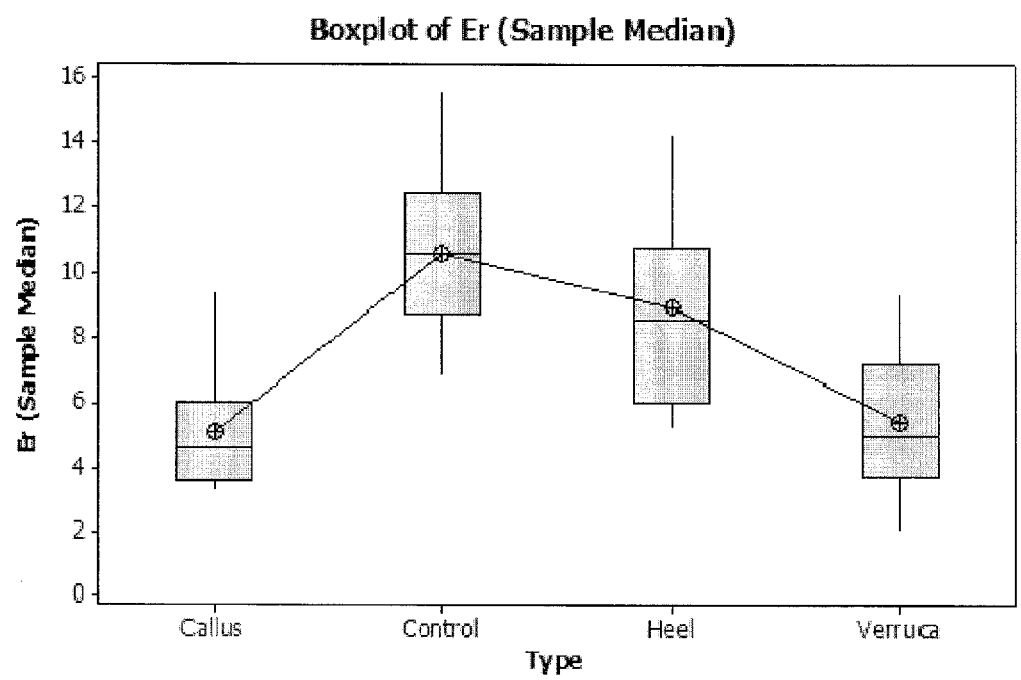
FIG. 9 is a schematic illustration of a comparison of the statistical analysis of sample medians of various plantar tissues for a sample population.

With reference to FIG. 9 a comparison of statistically analysed measurements of the dielectric properties of various plantar tissues over a sample population (using the median of the measurement range 7.5-8.5 GHz taken from each sample) is illustrated.

It will be understood that embodiments of the present invention have been described above purely by way of example, and modifications of detail can be made within the scope of the invention.

Each feature disclosed in the description, and (where appropriate) the claims and drawings may be provided independently or in any appropriate combination.

The invention claimed is:

1. A method of treating a viral lesion caused by human papillomavirus (HPV), said method comprising administering to a subject having said viral lesion caused by HPV, a therapeutically effective amount or dose of microwave energy to the lesion, wherein:
   the administering of the therapeutically effective amount or dose of microwave energy comprises using a delivery system to administer the therapeutically effective amount or dose of microwave energy via a microwave applicator to tissue of the subject that has said lesion caused by HPV; and the method comprises electrically matching the microwave applicator to the tissue that has said lesion caused by HPV, based on the tissue that has said lesion caused by HPV having a lower dielectric constant than a dielectric constant that said tissue would have if said tissue did not have said lesion caused by HPV, such that the microwave applicator is better matched to the tissue that has said lesion caused by HPV than it would have been if the said tissue did not have said lesion caused by HPV;

wherein the microwave energy is selected such as to expose antigenic sites stimulating a localized immune response at the lesion, and the administering of the therapeutically effective amount or dose of microwave energy to the lesion comprises repeatedly applying the microwave energy in a pulsed manner thus providing repeated rounds of localized hyperthermia at the lesion and repeated localized stimulation of the immune response at the lesion.

2. The method of claim 1, wherein the microwave energy has a frequency of at least one of:—
between about 500 MHz and about 200 GHz;
between about 900 MHz and about 100 GHz;
between about 5 GHz to about 15 GHz.

3. The method of claim 1, wherein the microwave energy has a frequency of about 8 GHz.

4. The method of claim 1 wherein the dose or amount of microwave energy at least one of produces, induces, elevates levels of heat shock factor HSF to stimulate production of a heat shock protein in or near the tissue.

5. The method of claim 4, wherein the heat shock protein is selected from the group consisting of HSP90, HSP72, HSP70, HSP65, HSP60, HSP27, HSP16 and any another heat shock protein(s).

6. The method of claim 4, wherein the microwave energy promotes an association between the elevated heat shock protein and the infected tissue so as to elicit an immune response against the infection.

7. The method of claim 1, said method comprising delivering the therapeutically effective amount or dose of microwave energy to the lesion, wherein the microwave energy at least one of cauterises, coagulates, shrinks, blocks, ablates, damages, irritates, inflames, otherwise interferes with the normal operation of the capillaries supplying blood to the lesion.

8. The method of claim 7, wherein the lesion is a skin lesion comprising at least one of a wart, verruca, benign growth, skin cancer resulting from a HPV infection.

9. The method of claim 1, comprising using as the microwave applicator a microwave applicator that would not optimally electrically match to said tissue if said tissue did not have said viral lesion caused by HPV.

10. The method of claim 1, wherein:—
said tissue has an epsilon relative value in a range from 2 to 10; and
the method comprises electrically matching to said tissue having an epsilon relative value in a range from 2 to 10,
wherein said epsilon relative value of said tissue in the range from 2 to 10 is lower than an epsilon relative value that said tissue would have if said tissue did not have said viral lesion caused by HPV.

11. The method of claim 1, wherein:—
said tissue has an epsilon relative value in a range from 4 to 6.7; and the method comprises electrically matching to said tissue having an epsilon relative value in a range from 4 to 6.7,
wherein said epsilon relative value of said tissue in the range from 4 to 6.7 is lower than an epsilon relative value that said tissue would have if said tissue did not have said viral lesion caused by HPV.

12. The method of claim 1, comprising selecting said microwave applicator from a set of disposable microwave applicators, wherein said selected microwave applicator has a lower dielectric constant than a dielectric constant that would match to said tissue if said tissue did not have said viral lesion caused by HPV.

13. An apparatus for use in treating a subject having a viral lesion caused by human papillomavirus (HPV), said apparatus comprising a microwave source for providing microwave energy and a delivery system for delivering a therapeutically effective amount or dose of the microwave energy via a microwave applicator to the lesion of the subject to be treated, wherein the microwave applicator is electrically matched to the tissue that has said lesion caused by HPV, based on the tissue that has said lesion caused by HPV having a lower dielectric constant than a dielectric constant that said tissue would have if said tissue did not have said lesion caused by HPV, such that the microwave applicator is better matched to the tissue that has said lesion caused by HPV than it would have been if the said tissue did not have said lesion caused by HPV wherein the microwave energy is selected such as to expose antigenic sites stimulating a localized immune response at the lesion, and the apparatus is configured to administer the therapeutically effective amount or dose of microwave energy to the lesion by repeatedly applying the microwave energy in a pulsed manner thus providing repeated rounds of localized hyperthermia at the lesion and repeated localized stimulation of the immune response at the lesion.

14. The apparatus of claim 13, further comprising at least one of:—
a controller for controlling at least one property of the microwave energy produced by the microwave source;
a monitor for monitoring the microwave energy produced by the microwave source.

15. The apparatus of claim 13, wherein the delivery system for delivering microwave energy electrically matches the range of epsilon relative values of the tissue affected by said viral lesion caused by HPV.

16. The apparatus of claim 13, wherein the delivery system for delivering the microwave energy to a subject comprises a component for contact with a subject to be treated.

17. The apparatus of claim 16, wherein the component is removable such that it can be discarded or sterilised after use.

18. The apparatus of claim 13, wherein the delivery system for delivering microwave energy is compatible with at least one of:—an internal body part; an external body part; a bodily surface; a lesion of an internal body part; a lesion of an external body part; a lesion of a bodily surface.

19. The apparatus of claim 13, wherein the microwave energy has a microwave treatment frequency, and the microwave treatment frequency is at least one of:—
in the range 500 MHz to about 200 GHz;
in the range about 900 MHz to about 100 GHz;
in the range about 5 GHz to about 15 GHz.

20. The apparatus of claim 13, wherein the microwave treatment frequency is 8 GHz.

21. An apparatus according to claim 13, wherein the microwave applicator is electrically matched to said tissue having an epsilon relative value in a range from 2 to 10.

22. An apparatus according to claim 13, wherein the microwave applicator is electrically matched to said tissue having an epsilon relative value in a range from 4 to 6.7.

\* \* \* \* \*